United States Patent [19]
Corriveau et al.

[11] Patent Number: 5,846,184
[45] Date of Patent: Dec. 8, 1998

[54] SWAGING OF A SHEATH TO A FIBER

[75] Inventors: André Corriveau, 6410 Fontaine Str., Rock Forest Qc, Canada, J1N 2S6; Aileen L. Murphy, Menlo Park, Calif.

[73] Assignee: André Corriveau, Rock Forest, Canada

[21] Appl. No.: 877,003

[22] Filed: Jun. 16, 1997

Related U.S. Application Data

[60] Provisional application No. 60/020,499 Jun. 7, 1996.
[51] Int. Cl.⁶ .................................................... A61B 1/06
[52] U.S. Cl. ........................ 600/160; 600/182; 600/920; 385/115
[58] Field of Search .................................... 600/160, 161, 600/182, 920; 385/115, 116, 117, 76, 84, 88

[56] References Cited

U.S. PATENT DOCUMENTS 4,986,622   1/1991   Martinez ............................. 600/182 X

*Primary Examiner*—Beverly M. Flanagan
*Attorney, Agent, or Firm*—Collard & Roe, P.C.L.

[57] ABSTRACT

A method of connecting a fiber-protective sheath to a fiber assembly having a fiber covered by a protective multi-layer skin, and the combination of the sheath and the fiber assembly. The skin has an inner cladding and an outer jacketing. The fiber-protective sheath extends externally around the fiber assembly and has at least one end externally swaged to a corresponding portion of the fiber assembly so that the inner cladding of the fiber assembly is not plastically deformed. The method comprises externally swaging at least one end of the sheath to a corresponding portion of the fiber assembly so that the innermost cladding of the fiber assembly is not plastically deformed.

6 Claims, 1 Drawing Sheet

SWAGING OF A SHEATH TO A FIBER

CROSS-REFERENCE

This application derives from provisional application Ser. No. 60/020,499 filed on Jun. 17, 1996.

BACKGROUND OF THE INVENTION a) Field of the Invention

The present invention relates to a method for connecting by swaging a sheath to a fiber assembly, especially an optical fiber assembly comprising a fiber covered by a protective double-layer skin including an inner cladding and an outer jacketing.

The invention also relates the combination of a fiber assembly of the above type with a sheath connected thereto by a swage, such combination being useful in particular in the medical field as a myoma coagulation fiber/sheath assembly, or as a laparoscopic probe.

b) Background of the Invention

In the papermaking industry, it is of common practice to use pintlepins to connect together looped ends of adjacent segments of endless belts. Such, a pintlepin usually comprises one or more filaments called "pintle", whose purpose is to close the seam defined by the intermeshed looped ends of the endless belt segments. It is also comprises a rigid or semi-rigid guidewire called "leader", whose purpose is to facilitate the insertion of the pintle through the intermeshed loops of the adjacent ends of the endless belt segments. The leader is rigidly connected to the pintle by means of metal sleeve or tubing called "swedger" or "swage", in which the rear end of the leader and the front end of the pintle are respectively swaged in line. Such a swaging is made in a press which is devised in such a manner as to apply a substantially uniform pressure radially all around the swage until it contracts and "pinches" the adjacent ends of the leader and pintle together.

In other technical fields such as the medical field, it is also of common practice to use probes or similar instruments which comprises an optical fiber having one end provided with a connector plug connectable to a laser source or any other optical equipment, and another end which is inserted in (viz. threaded through) a sheath made of rigid material whose purpose is essentially to make grasping, handling and orientation of this other end much easier and simpler, thereby facilitating the job of the operator, which, in the case of a laparoscopic probe is surgeon who carries out a medical step.

So far, the sheath is connected in proper position onto the fiber by crimp or adhesive bonding. Such is efficient but has a major drawback, especially when the bonding extend over the full length. Indeed, in such a case, cracks often occur when the probe or instrument is subject to ultrasonic cleaning, because of the difference in expansion between the sheath which is usually made of stainless steel, and the fiber which is usually made of glass.

SUMMARY OF THE INVENTION

It has now been found, and this is the object of the present invention, that instead of using crimp or adhesive bonding to connect the sheath to the fiber, use can efficiently be made of a swage as is used for the manufacture of pintlepins.

More particularly, it has been found that:

1—strong connection can be achieved between the sheath and fiber with a swage without damaging (cracking) the fiber when such fiber is covered, as is of common practice, by a protective multi-layer skin including an outer jacketing and an inner most cladding;

2—the swage does not interfere with the transmission quality of the optical fiber, provided that it is installed in such a manner as not to unduly plastically deform the inner most cladding; and 3—the sheath needs be swaged at one of its ends only, viz. its proximal end, as the "play" between the fiber and sheath at the distal end thereof is considered negligible in the performance of the instrument, especially by a surgeon.

Thus, the present invention provides a method for connecting together a fiber-protective sheath to a fiber assembly including a fiber covered by a protective multi-layer skin comprising an inner cladding and an outer jacketing, which method consists essentially in swaging with a swage at least one end of the sheath to a corresponding portion of the fiber assembly in such a manner that the inner cladding of the fiber assembly is not plastically deformed.

The invention also provides the combination of a fiber assembly of the above type with a sheath surrounding the assembly, wherein the sheath has at least one end connected to a corresponding portion of the fiber assembly by a swage that is swaged thereto in such a manner that the inner cladding of the fiber assembly is not plastically deformed.

Preferably, only one end of the sheath is swaged to the fiber assembly. However, both ends of the sheath could be swaged if such is needed.

Such a combination can be part of a laparoscopic probe or of any other instrument wherein one end of a glass fiber is threaded through a stainless steel sheath.

The invention will be better understood upon reading the following non-restrictive description made with reference to the accompanying drawings.

DESCRIPTION OF A PREFERRED EMBODIMENT OF THE INVENTION

Figure 1:
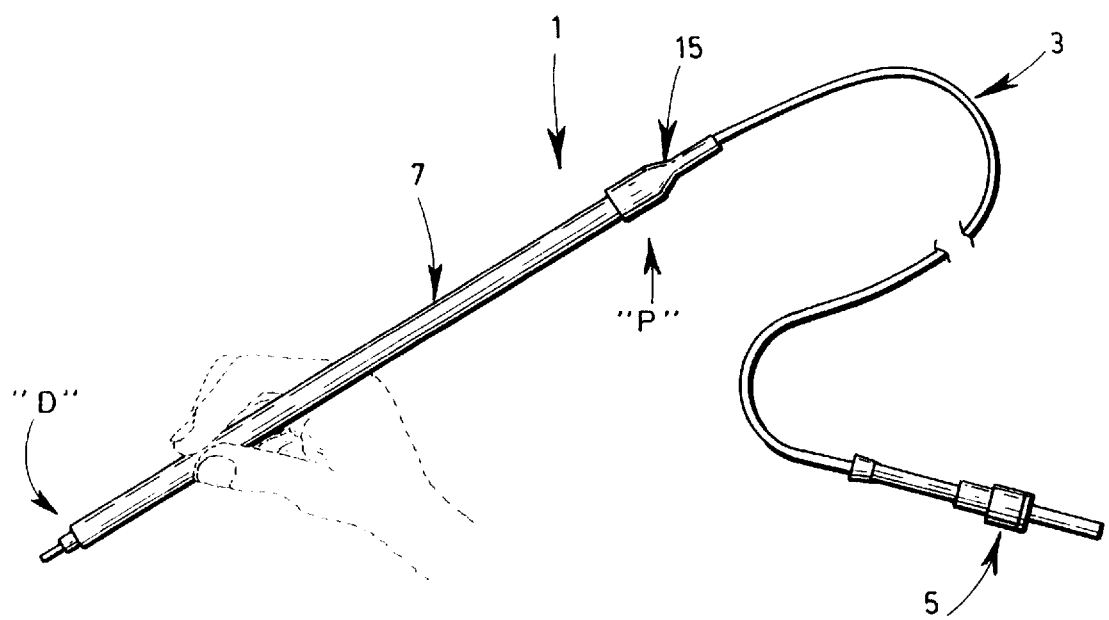
FIG. 1 is a schematic representation of a probe comprising a sheath swaged onto a fiber assembly according to the invention.

The probe 1 shown in FIG. 1 is a laparoscopic probe. It comprises a fiber assembly 3 connectable to a laser source (not sown) by means of connector plug 5. It also comprises a sheath 7 made of hypodermic stainless steel, through which the free end of the fiber assembly opposite to the plug 5 is threaded.

As was explained hereinabove, the basic purpose of the sheath is to facilitate hand-grasping, handling and orientation of the free end of fiber assembly by the operator, viz. the surgeon using the laparoscopic probe during an operation.

Figure 2:
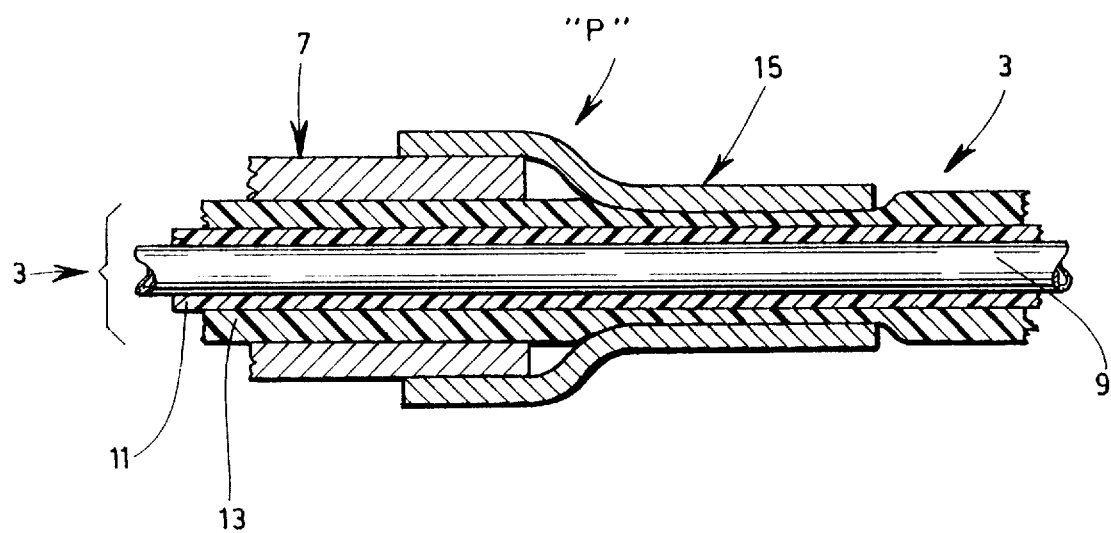
FIG. 2 is a cross-section view of the swage connecting the sheath to the fiber assembly of the probe shown in FIG. 1.

As is better shown in FIG. 2, the fiber assembly 3 comprises a glass fiber 9, which is covered by a protective multi-layer skin. In the illustrated embodiment, such skin comprises a thin inner cladding 11 preferably made of a fluoropolymer, and a thicker outer jacketing 13. This kind of fiber assembly 3 is known per se and available from different manufacturers under the tradenames RUTGER'S or POLYMICRO.

As is also shown in FIG. 2, the fiber assembly 3 has an outer diameter which is substantially equal to the inner diameter of the sheath 7, thereby reducing to a minimum extent the play that could exist between the same, especially at the distal end "D" of the sheath adjacent the "operative" end of the fiber.

In accordance with the invention, connection between the sheath 7 and the fiber assembly 3 passing therethrough is made with a metal tubing 15 called "swage", which is pressed (swaged) onto the proximal end "P" of the sheath 7 and the adjacent portion of the fiber assembly 3 in such a manner as to rigidly pinch these two elements together and prevent them from being removed non-destructively.

In accordance with a very important aspect of the invention, such a swaging of the sheath and fiber assembly is and must be carried out in such a manner that the inner most cladding 11 is not plastically deformed. In other words, such a swaging is carried out in such a manner that only the outer jacketing and intermediate layers, if any, are deformed, as is shown in FIG. 2.

If desired, a plastic coating (not shown) may be applied onto the swage 15 after its fixation to cover and protect it.

As aforesaid, it has surprisingly been discovered that:

1—strong connection can be achieved between the sheath 7 and the fiber assembly 3 with the swage 15 without damaging (cracking) the fiber 9 of the assembly when such fiber is covered, as is of common practice, by a protective double-layer skin including an outer jacketing 13 and an inner cladding 11;

2—the swage 15 does not interfere with the transmission quality of the optical fiber 9, provided that it is installed in such a manner as not to unduly plastically deform the inner cladding 11; and 3—the sheath 7 needs be swaged at one of its ends only, viz its proximal end, as the "play" between the fiber assembly 3 and sheath at the distal end thereof is considered negligible in the performance of the instrument, especially by a surgeon. However, the sheath could be swaged at both ends, if such is needed.

In a preferred yet not restrictive embodiment, the swage 15 is preferably made of a stainless steel tubing that is 0.75 to 1.00 inch long. The sheath 7 may be 17 to 18 inches long while the fiber assembly 3 may be up to 10 feet long. Preferably, the sheath is positioned in such a manner that about 0.5 inch of the fiber 9 protrudes beyond the distal end of the sheath. Such is rather conventional and needs not be further explained.

The probe 1 is preferably designed to be disposable. Thus, the use of a non-expansive, easy-to-install swage 15 to connect the sheath 7 to be fiber assembly 3 is of a great commercial interest.

As aforesaid, the invention is not restricted to this particular application and could actually be used for any other application whereas a sheath is to be connected onto a skin-covered fiber.

We claim:

1. A method for connecting together a fiber-protective sheath to a fiber assembly including a fiber covered by a protective multi-layer skin comprising an inner cladding and an outer jacketing, said method consisting essentially in swaging externally with a swage at least one end of the sheath to a corresponding portion of the fiber assembly in such a manner that the inner most cladding of the fiber assembly is not plastically deformed.

2. The method of claim 1, comprising swaging both ends of the sheath to the fiber assembly.

3. The combination of a fiber-protective sheath with a fiber assembly including a fiber covered by a protective multi-layer skin comprising an inner cladding and an outer jacketing, wherein the fiber-protective sheath extends externally around the fiber-assembly and has at least one end connected to a corresponding portion of the fiber assembly by a swage that is externally swaged thereto in such a manner that the inner cladding of the fiber assembly is not plastically deformed.

4. The combination of claim 3, wherein the swage consists of a stainless steel tubing that is 0.75 to 1.00 inch long.

5. The combination of claim 4, wherein the sheath is made of stainless steel.

6. The combination of claim 5, wherein said combination is part of a laparoscopic probe.

* * * * *